United States Patent [19]

Schoch

[11] Patent Number: 4,637,729
[45] Date of Patent: Jan. 20, 1987

[54] FIBER OPTIC MOISTURE ANALYSIS PROBE

[75] Inventor: Stephen A. Schoch, Liverpool, N.Y.

[73] Assignee: Carrier Corporation, Syracuse, N.Y.

[21] Appl. No.: 561,409

[22] Filed: Dec. 14, 1983

[51] Int. Cl.[4] ............................................. G01N 21/85
[52] U.S. Cl. .................................. 356/410; 250/227; 356/408; 356/436; 356/440
[58] Field of Search ............... 250/227, 339, 373, 565; 356/408, 409, 410, 411, 434, 435, 40, 41, 402, 418, 432, 436, 320

[56] References Cited

U.S. PATENT DOCUMENTS

| | | | |
|---|---|---|---|
| 3,733,130 | 5/1973 | Young | 250/227 |
| 3,740,155 | 6/1973 | Keller et al. | 356/409 |
| 3,843,226 | 10/1974 | Person | 356/320 |
| 3,853,407 | 12/1974 | Dewey, Jr. | 356/434 |
| 4,001,595 | 1/1977 | Reisman | 250/565 |
| 4,092,069 | 5/1978 | Fukuda et al. | 356/434 |
| 4,152,075 | 5/1979 | Rellstab et al. | 356/435 |
| 4,176,963 | 12/1979 | Fabinski et al. | 356/408 |
| 4,248,536 | 2/1981 | Hijikata | 356/434 |
| 4,498,781 | 2/1985 | Kaplit | 356/435 |
| 4,505,583 | 3/1985 | Konomi | 356/419 |
| 4,523,096 | 6/1985 | Yasuda et al. | 356/410 |

FOREIGN PATENT DOCUMENTS 0096429 7/1980 Japan ................................ 356/411

OTHER PUBLICATIONS

Levine et al., IBM Technical Disclosure Bulletin, vol. 18, No. 11 Apr. 1976, p. 3754.
Machine Design Article.
Takeo et al., Article in Japanese Journel of Applied Physics 10/82, vol. #21, No. 10, pp. 1509–1512.
Wilks, Jr., Article-Industrial Research & Development 9/82, pp. 132–135.

Primary Examiner—F. L. Evans
Assistant Examiner—Joel L. Harringa
Attorney, Agent, or Firm—David J. Zobkiw

[57] ABSTRACT

Light in two different wavelengths, only one of which is attenuated by the presence of a substance to be tested for, is passed through a light path which includes a fluid path. The two wavelengths are equally attenuated by particulate contamination and all other conditions except for the presence of the tested for substance. A light path through a reference cell provides a reference for each wavelength. The presence of the tested for substance provides a differential attenuation which is indicative of the presence of the substance and the degree of differential attenuation is a measure of the concentration of the substance.

4 Claims, 4 Drawing Figures

FIBER OPTIC MOISTURE ANALYSIS PROBE

BACKGROUND OF THE INVENTION

Optical fibers have been adapted to send information or energy along circuitous paths and over long distances. This is possible because the optical fibers are provided with a cladding which greatly reduces attenuation of the optical signal by internally reflecting incident light. Attenuation has, however, been employed to adapt optical fibers as sensors. To this end, the cladding is removed from a length of the optical fiber which is bent one or more times in the unclad length. A bend results in an increased angle of incidence and this together with the absence of cladding causes a portion of the incident light to be transmitted into the surrounding medium rather than being essentially totally reflected. The amount of light transmitted into the surrounding medium is dependent upon the physical characteristics of the surrounding medium and this phenomenon has been employed to determine a characteristic of the surrounding medium such as by determining concentration or detecting the presence of a particular substance in the surrounding media. This type of testing requires that the stripped section of optical fiber physically contact the medium to produce the required attenuation indicative of the presence of the substance. Unfortunately, substances such as oil tend to coat the stripped surface after initial contact and it is this interface which determines the degree of attenuation. As a result these devices are unsuitable for long term monitoring unless the probe is frequently removed for cleaning of contaminants and the accuracy of the device can be compromised by contaminants during the periods between cleanings.

SUMMARY OF THE INVENTION

The present invention is directed to a fiber optic moisture analysis probe in which the light paths are, in part, through the medium to be tested/monitored or a standard. The light paths are essentially axial through the fiber to a normal termination which is spaced from a reflecting surface by a space which is in fluid communication with the medium to be tested/monitored or contains a reference medium sealed therein. Because light at different wavelengths often has different optical properties due to the presence of a substance in a medium, in each light path, light is supplied in two different wavelengths one of which is affected by the substance to be tested for and one of which is not. The unaffected wavelength serves as a reference and cancels out any losses due to the presence of contaminants. Alternatively, light is supplied over a spectrum that includes the two different wavelengths. The device is pressure and temperature dependent only to the extent that they affect the density of the fluid being tested/monitored.

It is an object of this invention to provide a fiber optic moisture analysis probe which is suitable for continuous long term use without requiring cleaning.

It is a further object of this invention to provide a fiber optic probe which includes a portion of the medium to be tested/monitored as a part of the optical path.

It is a still further object of this invention to provide a fiber optic probe suitable for detecting moisture in refrigerant vapor and liquid as well as in mineral oils used for compressor lubrication.

It is another object of this invention to provide a fiber optic probe suitable for detecting oil concentration in the chiller of a refrigeration system.

It is an additional object of this invention to provide a probe which can be located remotely from the power source and detectors.

It is a further object of this invention to provide a method for continuously optically monitoring/testing fluids independent of the presence of contamination. These objects and others as will become apparent hereinafter, are accomplished by the present invention.

Basically, two different wavelengths of light, individually or as part of a light spectrum, are transmitted through two optical fibers. The light passes from an end of a fiber through the medium to be tested/monitored or the reference medium then impinges upon the concave surface of a mirror and is reflected back through the medium and back into the fiber. Depending upon contamination and the presence of the tested for substance, attenuation of one or both of the wavelengths takes place in the medium to be tested/monitored. If the attenuation is due to contamination, variation in light source etc., both wavelengths are attenuated equally and subsequently cancelled out. However, where only one of the wavelengths is affected by the presence of the tested for substance, the difference in attenuation is a measure of the presence of the substance. For example, light in the 2.8 to 3.1 micron wavelength is attenuated by substances having an oxygen-hydrogen, O—H, bond such as water, alcohols, glycols and organic acids, which can then be detected in fluids without such bonds, such as halocarbon refrigerants like the Freons, and refined mineral oils used for lubrication.

BRIEF DESCRIPTION OF THE DRAWINGS

For a fuller understanding of the present invention, reference should now be made to the following detailed description thereof taken in conjunction with the accompanying drawings wherein.

DESCRIPTION OF THE PREFERRED EMBODIMENT

Figure 1:
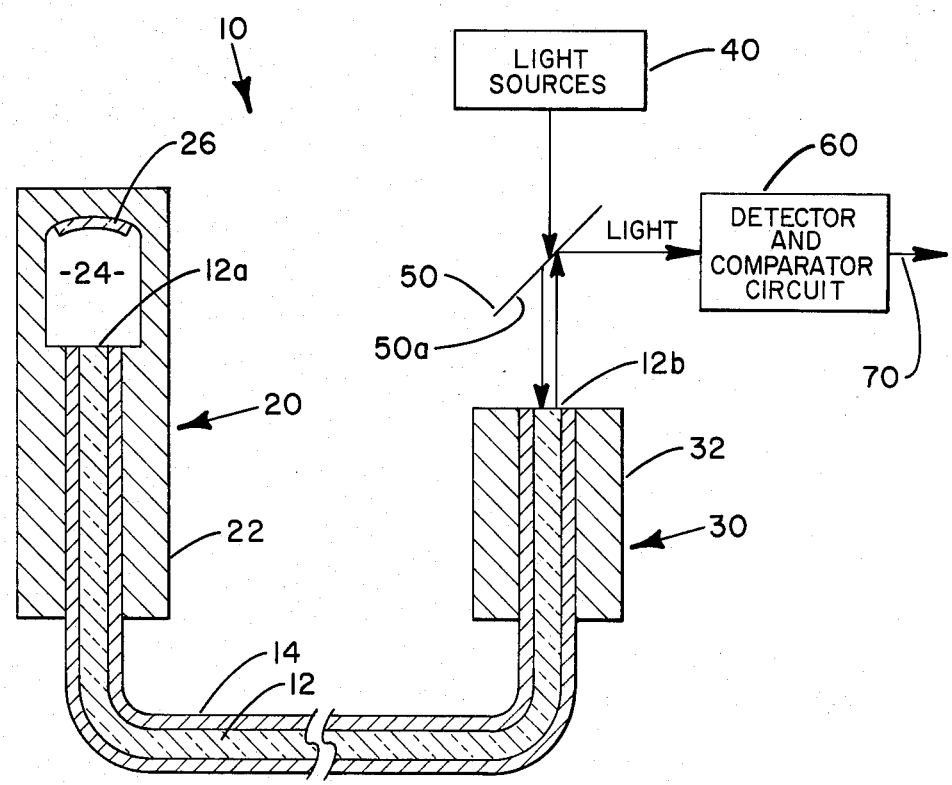
FIG. 1 is a partially sectioned schematic representation of the test cell of the fiber optic probe of the present invention.

In FIG. 1, the numeral 10 generally designates the test cell portion of a fiber optic probe including an optical fiber 12 surrounded by a sheath and cladding 14 and having a probe end 20 and a source/detector end 30. Probe end 20 includes a test probe body 22, typically machined from a ½ inch diameter epoxy rod, encasing a first end of fiber 12 and defining an opening or fluid passage 24. A circular concave mirror 26 forms one wall of the fluid passage 24 and is directly opposite the termination 12a of fiber 12. Termination 12a is normal to the axis of fiber 12. Source/detector end 30 includes a plastic sheath 32 encasing a second end of fiber 12 and adapted to permit the securing of end 30 in a fixed position. Termination 12b of fiber 12 is normal to the axis of fiber 12.

Figure 2:
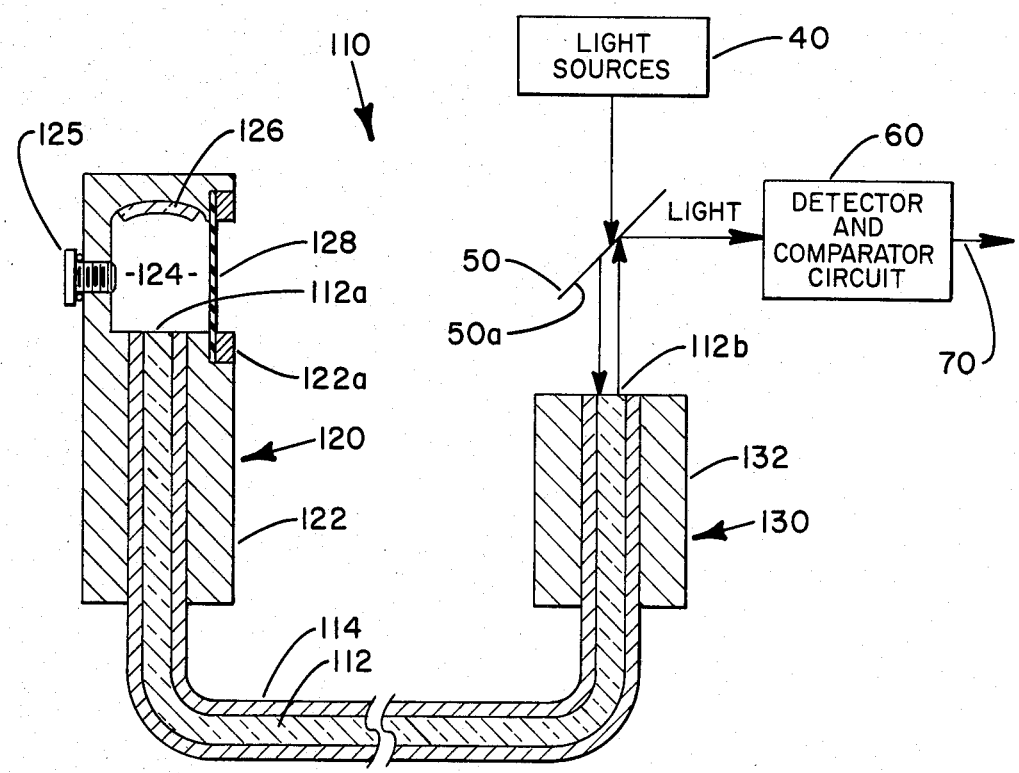
FIG. 2 is a partially sectioned schematic representation of the reference cell of the fiber optic probe of the present invention.

In FIG. 2, the numeral 110 generally designates the reference cell portion of a fiber optic probe including an optical fiber 112 surrounded by a sheath and cladding 114 and having a probe end 120 and a source/detector end 130. Probe end 120 includes a reference probe body 122 encasing a first end of fiber 112 and defining a sealed chamber 124. A threaded plug 125 permits the charging of chamber 124 with a reference medium and then sealing the chamber 124. A circular concave mirror 126 forms one wall of the sealed chamber 124 and flexible diaphragm 128 forms another. Mirror 126 is directly opposite the termination 112a of fiber 112 and termination 112a is normal to the axis of fiber 112. Diaphragm 128 is attached/sealed to probe body 122 in any suitable manner as by gluing in place and overlying diaphragm 128 with a portion 122a of the material removed from body 122, or the equivalent, suitably secured to diaphragm 128 and body 122 as by gluing, screws, etc.

Light sources 40 provide light at two wavelengths for both the test cell 10 and the reference cell 110. The light may be provided simultaneously at both wavelengths or the wavelengths may be alternated. The light sources 40 may be tunable lasers, unfiltered incandescent light including the two wavelengths or incandescent light filtered to transmit only the two wavelengths or any other suitable source. The light sources 40 have two outputs that are essentially axially aligned with fibers 12 and 112 and normal to terminations 12b and 112b so that there is essentially no refraction of light entering and leaving fibers 12 and 112. A half-silvered mirror 50 is in the optical paths between light sources 40 and terminations 12b and 112b and is inclined relative thereto. A half-silvered mirror permits a partial transmission and a partial reflection of incident light. Detector and comparator circuit 60 includes detectors and comparators with the detectors positioned to receive light from fibers 12 and 112 incident on and reflected from surface 50a of half-silvered mirror 50.

Figure 3:
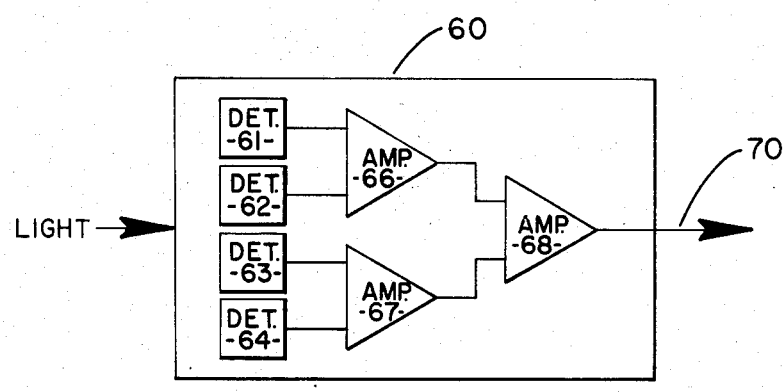
FIG. 3 is a detailed schematic of the detector and comparator circuit.

Referring now specifically to FIG. 3, the detector and comparator circuit 60 includes four detectors, 61-64, and three differential amplifiers 66-68 which are, typically, three of the four amplifiers of a quad operational amplifier such as model LM324N manufactured by National Semiconductor. The detectors 61-64 can be photo-Darlington transistors which are specific to the wavelengths of interest or may be non-specific detectors with filters located between mirror 50 and the detectors 61-64 to transmit only the wavelength of interest to the detectors 61-64. The detectors 61-64 preferably have a battery supplied bias current so that all detectors equally reflect changes in the battery output.

These devices supply a voltage signal in response to incident light absorption at wavelengths corresponding to those wavelengths in which the device is designed to operate. Detectors 61 and 63 receive light passing from reference cell 110 while detectors 62 and 64 receive light passing from test cell 10.

Figure 4:
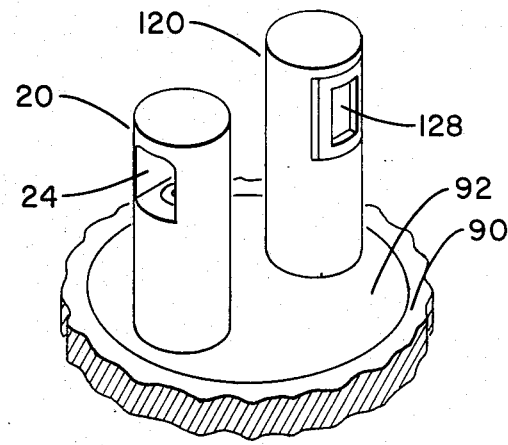
FIG. 4 is a pictorial view showing the test and reference cells in place.

In operation, as best shown in FIG. 4, probe ends 20 and 120 are suitably secured directly in the casing 90. Alternatively, probe ends 20 and 120 may be made integral with a plug or body 92. The probe ends 20 and 120, or plug 92 integral therewith, are secured in a device such as a chiller as by epoxying in place or by threading body or plug 92 into a mating threaded hole or pipe connection such that a portion of the fluid in the device passes through opening or fluid passage 24. Because probe end 120 is at essentially the same location as probe end 20, it is at the same temperature. Also, because the reference medium in chamber 124 is separated from the medium being monitored/tested in passage 24 by flexible diaphragm 128, the diaphragm 128 is able to flex to equalize the pressure in chamber 124 with that of the medium being tested/monitored but without blocking any portion of the light path across chamber 124. As a result, the pressure and temperature and thereby the density conditions are essentially identical in passage 24 and chamber 124. Since infrared light is attenuated by moisture (specifically substances having oxygen-hydrogen bonds) while visible light is not, to detect the presence of moisture, light sources 40 supply light in the visible range and in the 2.8 to 3.1 micron wavelength band. To detect the quantity of other compounds in various fluids, a wavelength must be selected such that the attenuation caused by the minor component, or constituent of interest is substantially greater than the attenuation caused by the major or bulk component. The light may just be in these two wavelengths, in a spectrum containing these wavelengths or the spectrum may be filtered so that only these wavelengths of interest are transmitted. The visible wavelength is selected such that its attenuation is dependent upon the contamination level and is not affected by the presence of moisture or some other constituent being analyzed. The fluid must also be substantially transparent to this wavelength so as to allow an adequate light level to energize detectors 63 and 64 reliably.

The light serially passes through half-silvered mirror 50 with a loss that cancels out for the two wavelengths, through fibers 12 and 112 entering at terminations 12b and 112b, respectively, and leaving at terminations 12a and 112a, respectively. The light then passes across fluid passage 24 and chamber 124, respectively. Both wavelengths are equally attenuated by contamination in passage 24, but only the infrared light is attenuated by the presence of moisture. The light impinges upon the concave mirrors 26 and 126, respectively, and is reflected back across fluid passage 24 and chamber 124, respectively. The infrared light is further attenuated by the presence of moisture in passage 24. In the case of reference cell 110, there should be no moisture present or else moisture should only be present in the desirable amount. Likewise, there should be no contamination present. Depending upon the degree of the differential attenuation which is a measure of the moisture present in passage 24 with the effects of contamination cancelled, infrared light and visible light enter termination 12a, pass through fiber 12 and leave at termination 12b. Similarly, infrared light and visible light reflected by mirror 126 enter termination 112a, pass through fiber 112 and leave at termination 112b. The light leaving terminations 12b and 112b then impinges upon surface 50a of half-silvered mirror 50, at spaced locations. Mirror 50 reflects a portion of all incident light and the reflected light impinges upon detectors 61-64 which furnish voltage signals representative of the incident light to comparators 66-68. More specifically, detectors 61 and 62 are either specific to one affected wavelength, or band of wavelengths, or the incident light is filtered between mirror 50 and detectors 61 and 62 such that only the wavelength, or band of wavelengths, of interest are incident on non-specific detectors 61 and 62. The light incident on detector 61 is from reference cell 110 and produces a reference signal which is the base line value for moisture and is supplied as a positive input to differential amplifier 66. The light incident on detector 62 is the current value for light transmitted through the probe or test cell 10 that is subject to attenuation from both moisture and contaminants and is supplied as a positive input to differential amplifier 66. In amplifier 66 the difference between the reference signal voltage supplied by detector 61 and the test signal voltage from detector 62 is produced as an output representing the attenuation due to both moisture and contamination and is supplied as a positive reference input to amplifier 68. The detectors 63 and 64, also, are either specific to one unaffected wavelength, or band of wavelengths, or the incident light is filtered between mirror 50 and detectors 63 and 64 such that only the wavelength, or band of wavelengths of interest are incident on non-specific detectors 63 and 64. The light incident on detector 63 is from reference cell 110 and produces a reference signal which is the base line reference for attenuation due to contamination and is supplied as a positive input to differential amplifier 67. The light incident on detector 64 is the current value for light transmitted through the probe or test cell 10 that is subject to attenuation only from contamination and is supplied as a positive input to differential amplifier 67. In amplifier 67 the difference between the reference signal and the signal voltage from detector 64 is produced as an output representing the attenuation due only to contamination and is supplied as a positive voltage input to differential amplifier 68. Differential amplifier 68 subtracts the inputs which cancel out the effects of contamination since it affects all wavelengths. The difference is supplied to the line 70 and represents the attenuation due to moisture and can be both a qualitative and quanitative value when processed in any well known conventional manner, such as analog or digital conversion to actual moisture concentration values using state-of-the-art microprocessor technology.

From the foregoing it should be obvious that both wavelengths are equally affected by losses in passing through the half-silvered mirror 50 and the presence of contaminants in the flow path 24, particularly on mirror 26. However, only one properly selected wavelength is attenuated by the presence of the tested for substance, moisture/oil, and this difference in attenuation is an indication of the presence of the substance and the degree of attenuation is a measure of the concentration of the tested for substance. The output in each wavelength is compared to a reference to determine the attenuation in that wavelength. Then the results are compared to cancel the effects of contamination and to obtain an indication of the tested for substance.

Although a preferred embodiment of the present invention has been specifially described and illustrated in terms of a moisture sensor, the selection of other combinations of wavelengths permit the sensing of other substances and therefore other changes will occur to those skilled in the art. Additionally, passage 24 and chamber 124 could be in the same housing and merely separated by a flexible diaphragm to ensure the same pressure and temperature in each. Alternatively, they could be mounted in a member which was, in turn, located in the device to be tested. Also, the fiber optic cables could be located in a common sheath. Similarly, source/detector ends 30 and 130 and thereby terminations 12b and 112b can be in the same casing or they may be separated any appropriate distance. The light sources 40 can supply light to the separated fibers 12 and 112 via a beam splitter or any other suitable arrangement and this, in turn, would further separate the light supplied to detectors 61 and 63 from that supplied to detectors 62 and 64. The reference cell 110 could be eliminated if corresponding voltage inputs were supplied to replace those supplied by detectors 61 and 63. It is therefore intended, that the scope of the present invention is to be limited only by the scope of the appended claims.

What is claimed is:

1. A probe for detecting the presence of a substance in a fluid comprising:
   first body means to be sealingly secured in the wall of a casing containing a fluid to be tested;
   a passage through said first body means defining a flow path;
   first mirror means forming a portion of said passage;
   first optical fiber means having one end received in said first body means and defining a first termination which is located across said passage from said first mirror means and forming a portion of said passage;
   said first optical fiber means having a second end defining a second termination;
   second body means to be sealingly secured in the wall of a casing containing a fluid to be tested;
   a sealed chamber in said second body means containing a reference medium;
   means for equalizing pressure in said sealed chamber with the pressure acting on said second body means;
   second mirror means forming a portion of said sealed chamber;
   second optical fiber means having one end received in said second body means and defining a first termination which is located across said sealed chamber from said second mirror means and forming a portion of said sealed chamber;
   said second optical fiber means having a second end defining a second termination;
   means for supplying light in a first wavelength which is attenuated in the presence of said substance and in a second wavelength which is not attenuated in the presence of said substance such that said light traverses a first path serially including said first optical fiber means from said second termination to said first termination, across said flow path where said light in said first wavelength is subject to attenuation due to the presence of said substance whereupon said light is reflected by said first mirror means and said light in said first wavelength is subject to further attenuation due to the presence of said substance and depending upon the attenuation said light enters said first termination of said first optical fiber means, passes through said first optical fiber means and out said second termination of said first optical fiber means and for supplying light in said first and second wavelengths to a second path serially including said second optical fiber means from said second termination to said first termination, across said sealed chamber to said second mirror means whereupon said light is reflected by said second mirror means and enters said first termination of said second optical fiber means, passes through said second optical fiber means and out of said second termination of said second optical fiber means; and means for detecting the amount of light in both of said wavelengths passing out of each of said second terminations.

2. The probe of claim 1 further including means for determining the difference in the amount of light in each of said wavelengths detected from each of said optical fiber means and for comparing the differences whereby an indication of the presence of the substance to be detected is obtained as well as an indication of the concentration thereof.

3. A probe for detecting the presence of a substance in a fluid comprising:
   body means to be sealingly secured in the wall of a casing containing a fluid to be tested;
   a passage through said body means defining a flow path therethrough;
   a sealed chamber in said body means containing a reference medium;
   means for equalizing the pressure of said reference medium with the pressure of the fluid to be tested;
   mirror means in said passage and said sealed chamber and forming a portion thereof;
   first optical fiber means having one end in said body means and defining a first termination which is located across said passage from said mirror means in said passage;
   second optical fiber means having one end in said body means and defining a first termination which is located across said sealed chamber from said mirror means in said sealed chamber;
   said first and second optical fiber means each having a second end defining a second termination;
   means for supplying light in a first wavelength which is attenuated by said substance and in a second wavelength which is not attenuated in the presence of said substance;
   said means for supplying light in said first and second wavelengths supplies said light in said first and second wavelengths to said first and second optical fiber means at said second terminations;
   light supplied to said second termination of said first optical fiber means traverses a path serially including said first optical fiber means from said second termination to said first termination, across said flow path where said light in said first wavelength is subject to attenuation due to the presence of said substance whereupon said light is reflected by said mirror means in said passage and said light in said first wavelength is subject to further attenuation due to the presence of said substance and depending upon the attenuation said light enters said first termination, passes through said first optical fiber means and out said second termination;
   light supplied to said second termination of said second optical fiber means traverses a path serially including said second optical fiber means from said second termination to said first termination, across said sealed chamber whereupon said light is reflected by said mirror means in said sealed chamber across said sealed chamber and enters said first termination, passes through said second optical fiber means and out said second termination;
   means for detecting the amount of light in each of said wavelengths passing out of each of said second terminations; and
   means for directing all of said light passing out of said second terminations onto said means for detecting.

4. The probe of claim 3 further including means for determining the difference in the amount of light in each of said wavelengths passing out of each of said paths and for comparing the differences whereby an indication of the presence of the substance to be detected is obtained as well as an indication of the concentration thereof.

* * * * *